United States Patent [19]

Poggie et al.

[11] Patent Number: 5,167,372
[45] Date of Patent: Dec. 1, 1992

[54] APPARATUS AND PROCESS FOR REDUCING SIZE AND MOISTURE CONTENT OF MATERIALS

[76] Inventors: Joseph L. Poggie, 815 Iris La., Vero Beach, Fla. 32963; Robert A. Poggie, P.O. Box 860, Station B, Nashville, Tenn. 37235

[21] Appl. No.: 770,040
[22] Filed: Oct. 2, 1991
[51] Int. Cl.$^5$ .............................................. B02C 11/08
[52] U.S. Cl. ....................................... 241/23; 241/24; 241/57; 241/65; 422/309
[58] Field of Search ........................ 241/23, 24, 57, 65; 34/12, 60; 422/309

[56] References Cited

U.S. PATENT DOCUMENTS

| | | | |
|---|---|---|---|
| 1,821,639 | 9/1931 | Hiller | 422/309 X |
| 2,873,663 | 2/1959 | Hawk et al. | 241/65 X |
| 3,462,086 | 8/1969 | Bertrand et al. | 241/23 X |
| 3,687,749 | 8/1972 | Reinhall | 241/23 X |
| 3,761,024 | 9/1973 | Schwey et al. | 241/33 |
| 3,823,877 | 7/1974 | Poggie | 241/19 |
| 3,983,261 | 9/1976 | Mendoza . | |
| 4,145,007 | 3/1979 | Jetzer . | |
| 4,227,653 | 10/1980 | Jetzer . | |
| 4,239,160 | 12/1980 | Hawkins et al. . | |
| 4,428,535 | 1/1984 | Venetucci . | |
| 4,463,022 | 7/1984 | Sterner et al. . | |
| 4,749,133 | 6/1988 | Saylor et al. | 241/57 X |

*Primary Examiner*—Douglas D. Watts
*Attorney, Agent, or Firm*—Arnold, White & Durkee

[57] ABSTRACT

Apparatus and process for simultaneously milling, dehydrating and/or sterilizing a material by introducing the material into a chamber comprising rotating instruments while substantially simultaneously introducing a hot gas into the chamber. Gas and material are introduced tangentially to the chamber at points opposed from each other, and the gas and material both enter the chamber in the same direction as the rotating instruments.

27 Claims, 3 Drawing Sheets

APPARATUS AND PROCESS FOR REDUCING SIZE AND MOISTURE CONTENT OF MATERIALS

BACKGROUND OF INVENTION

1. Field of the Invention

This invention relates to an improved process and apparatus for simultaneously milling, drying and/or sterilizing a material into a powder or flakes of a desired size, moisture content, and degree of sterilization. This invention also relates to removal of undesired elements or compounds from a material by vaporization or thermal destruction.

2. Prior Art

Generally, four types of dehydrators have been used in industry. The first type of dehydrator is a rotating drum dehydrator which comprises a long tube that is heated and rotated simultaneously. Raw material such as fish scraps from commercial processing of crabs, fish, shrimp, etc. is introduced at one end and is heated and ground while it travels the length of the tube. The material ultimately emerges from the opposite end as a roughly ground powder. This rough powder is then ground to the desired size in a conventional hammermill.

A disadvantage of the rotating drum dehydrator is that vital elements such as proteins in the raw material tend to be destroyed. The rotation tube or drum contains pieces of material ranging from large pieces of raw material to small particles of finished dry material. As a result, the raw material is present in a wide range of volume-area ratios and it is difficult to provide optimum drying conditions for all material in the tube or drum. The heat absorption rate of the large pieces is limited by their low area-volume ratio, and the small particles are rapidly dried because of their high area-volume ratio. Thus the heat transfer rate to the large pieces is generally only increased by increasing the temperature of the air or the drum surface, or by increasing the air velocity. Unfortunately, if the air or surface temperatures are elevated, the small particles may be burned or charred. Burning and charring are undesirable and tend to destroy the vital elements sought to be retained in the finished product (e.g., proteins). Similarly, increasing the air velocity generally requires that the air volume also be increased, with attendant loss of efficiency.

Even at optimum conditions with this arrangement, experience has shown that the processing time for most material is several hours. This long processing time generally results in the destruction of heat sensitive protein, vitamins, and nitrates in addition to general burning of the material. In addition, long processing time may often encourage bacteria growth.

The second type of dehydrator grinds the raw material to medium sized pieces. These medium sized pieces are then heated and ground to a pulp, and the pulp is finally mixed with hot air to reduce it to a powder.

This device is a partially successful attempt to overcome the drawbacks of the rotating drum arrangement. By separating the grinding and drying operations, charring is largely eliminated. Nevertheless, the heat transfer rate is generally low because the air velocity relative to the material is low even though the absolute velocity of the heated air is high. The net result is that the machine is generally large, the processing time long, and the heat-sensitive protein may be destroyed because of long exposure to heat. The efficiency of this method also tends to be low.

The third and fourth types of dehydrators operate at high speed and high temperatures and generally grind and dry materials quickly and simultaneously.

In the third type of dehydrator, hot, dry air and the material to be processed are introduced into a mill in a radial direction at one end and the finished powder or meal, vapors, and air are withdrawn through an annular opening around the shaft at the other end of the mill. The mill contains a rotating shaft with blunt hammers or instruments attached. The hot, dry air is usually provided by a refractory furnace. The material is ground and dried in the mill under turbulent conditions. The turbulence, in combination with the action of the exhaust fan at the mill exit, provides the means of separating the finished product from the unfinished material so that the finished product may be withdrawn from the mill.

A disadvantage inherent in the third type of dehydrator is that the magnitude of the aerodynamic forces that may be generated by the hot air on the particles passing through the hot air are limited by practical considerations such as air density and air inlet velocity. The air inlet velocity, in turn, is limited by the pressure gradient that can be generated by an exhaust fan. Limitation of the aerodynamic forces also places a corresponding limitation on the centrifugal forces that may be tolerated in the mill. Consequently, the mill size, speed, and power inputs are limited because the device cannot function if the centrifugal forces are so great that it is impossible for aerodynamic forces to overcome them.

The fourth type of dehydrator is a modified version of the third type but the air enters the mill tangent to, and in the same direction of motion as the rotating hammers or instruments. The raw material enters the mill tangent to, and in a direction that is opposite to the motion the rotating instruments. An example of fourth type of dehydrator is described in U.S. Pat. No. 3,823,877 to Poggie.

The disadvantages of this apparatus are:

A. Some of the raw material entering the mill is generally burned or charred because some of it tends to immediately contact high temperature hot gas upon entering the chamber.

B. Some of the raw material entering the mill is generally forced back into the inlet by the rotating mill instruments.

C. The hot air entering the mill from the furnace is generally limited to about 950° F. (about 510° C.) (because a higher temperature results in an unacceptable level of ash in the finished material) resulting in low volumetric efficiency and low thermodynamic efficiency of the mill and of the furnace.

D. The furnace liner generally requires about one hour to reach a stabilized operating temperature, and as a result:

(1) the machine does not generally reach full capacity for about one hour after starting, and (2) the moisture content of the finished product exiting the mill does not generally stabilize at the desired moisture percentage for about one hour after the machine starts.

E. The high specific heat and low thermal conductivity of the refractory liner causes the response time of the furnace (to variations in raw material temperature, consistency, or moisture content) to be long, thus resulting in over-compensation in the furnace fuel system.

F. The high specific heat and low thermal conductivity of refractory liner in the furnace generally results in a long cool-down period after the machine is shut down. This long cool-down generally causes heavier fuel elements to "coke up" and clog the fuel nozzles and strainers. The clogging of the nozzles generally result in poor temperature regulation, diminished machine capacity, and frequent shut down time to clean the nozzles.

The above-described dehydrators have not proven to be entirely satisfactory for a variety of reasons. In addition to the above described limitations, the first two types usually require that the material be extensively pre-cooked and pressed to remove excess water and oil. This pre-cooking tends to destroy many of the vital elements in the material because of exposure to high heat for a relatively long period of time. In addition, many of dehydrators presently known are large, expensive, and costly to maintain and operate. Furthermore, processing time for the dehydrators presently known is also substantial, and thus the yield of the finished product, per unit time, from these devices is relatively small.

SUMMARY OF THE INVENTION

It is the general objective of the present invention to provide an improved apparatus and process for optimizing the drying and grinding process for converting any material, especially organic material such as fish scraps or grain, into clean, dry, sterilized powder, meal or flakes.

This objective may be accomplished with a chamber for milling, drying, or sterilizing a material which includes at least one rotatable instrument(s) extending radially from an axially extended drive shaft and operable to reduce the size of the material during use. In addition, the chamber includes a first inlet connected to supply material during use tangential to the chamber such that the material enters the chamber during use moving in the same direction as the instrument(s), and a second inlet connected to supply hot gas during use tangential to the chamber such that gas enters the chamber during use moving in the same direction as the instrument(s). Lastly, the chamber includes an outlet orifice surrounding the shaft for allowing material to exit the chamber, and wherein the orifice has a smaller diameter than the chamber.

Preferably the chamber is substantially cylindrical. The first inlet is preferably located adjacent to one end of the chamber and the second inlet extends substantially along the length of the chamber. In addition, preferably the first inlet is connected opposite of the second inlet to maximize mixing of the feed material (with material and gas in the chamber) prior to contacting the feed material with hot gas.

The chamber may further include an exhauster for withdrawing gas and material from the chamber during use. The exhauster is preferably located on the opposite end of the chamber from the first inlet.

An electric motor preferably powers the drive shaft of the chamber, and the flow rate of material to the chamber is preferably varied as a function of power used by the electric motor.

Preferably the orifice size is variable to enable the operator to easily vary the moisture content and/or size of the material particulate exiting the chamber. As the orifice size is decreased, then the particle sizes and moisture content of such particles tend to decrease (and vice versa). Preferably the apparatus includes a moisture sensor and/or particulate size sensor connected to sense the moisture content and/or size of the material that exits the orifice, the exhauster, or the system. The orifice size is then variable as a function of exiting material moisture content and/or size.

The chamber may also include a gas source for providing the hot gas which comprises a combustion section with a burner device at a first end and an outlet at a second end connected for flow of hot gas from the gas source to the second inlet of the chamber, and a first outer shell which substantially surrounds the combustion section and is separated from the combustion section by an air passageway. The shell usually includes an inlet on a first end for flow of ambient air into the air passageway, and an outlet on a second end for flow of air from the air passageway to the second inlet of the mill chamber.

The shell tends to increase the gas source efficiency by capturing heat in the air passageway that would otherwise be lost to the surroundings. The shell may be used in conjunction with a thermal radiation shield between the chamber and the shell, and/or surrounding the shell. Like the shell, the shield includes an air passageway connected to allow flow of ambient air to the chamber inlet. The shield tends to reflect most of the thermal radiation and transforms the remainder of the radiation into conductive and convective heat which may then be carried away by the air in the air passageways.

Preferably some, most, or all of the gas source is made from materials which have a relatively low specific heat and high thermal conductivity. If the gas source has a low specific heat and high thermal conductivity, it tends to heat up, cool down, and respond to operating conditions quicker. Furthermore, the gas source burners do not clog or "coke up" as quickly because the gas source heat tends to be quickly dissipated when turned off, thus preventing residual heat from causing light hydrocarbons in the fuel to vaporize, leaving heavier hydrocarbons to "coke up" the burners.

In addition to the apparatuses described above, the process of the invention includes tangentially introducing material into a chamber including at least one rotating instrument(s) such that the material enters the chamber moving in the same direction as the instruments, and tangentially introducing hot gas into the chamber such that the gas enters the chamber moving in the same direction as the instruments and the material is dried and reduced in size by contacting the hot gas and the instruments.

Features of this invention may include:
A. Providing an improved process and apparatus for processing organic material while preventing deterioration of the vital elements in the material.
B. Processing any material, including organic material, in a single, high speed operation.
C. Processing material into clean, dry, sterilized powder, meal, pellets, or flakes that are low in ash, high in digestibility, and low in bacteria count.
D. The air inlet to the mill is located such that hot air enters the mill tangent to, and in the same direction as, the motion of the extremities of the rotating mill instruments. Thus the main exhauster needs only to overcome the fan effect of the mill (but not the centrifugal effect of the rotating particles within the mill).

E. Rapidly moving mill instruments do not tend to force the raw material back into the feed mechanism.

F. The incoming hot air does not impinge on, overheat, char, or burn the raw material entering the chamber.

G. The moisture content and particle size of the finished product may be maintained within desired preselected limits.

H. The system operates with increased thermal efficiency, reduced maintenance, and improved temperature control over prior art devices.

DESCRIPTION OF THE PREFERRED EMBODIMENTS

Figure 1:
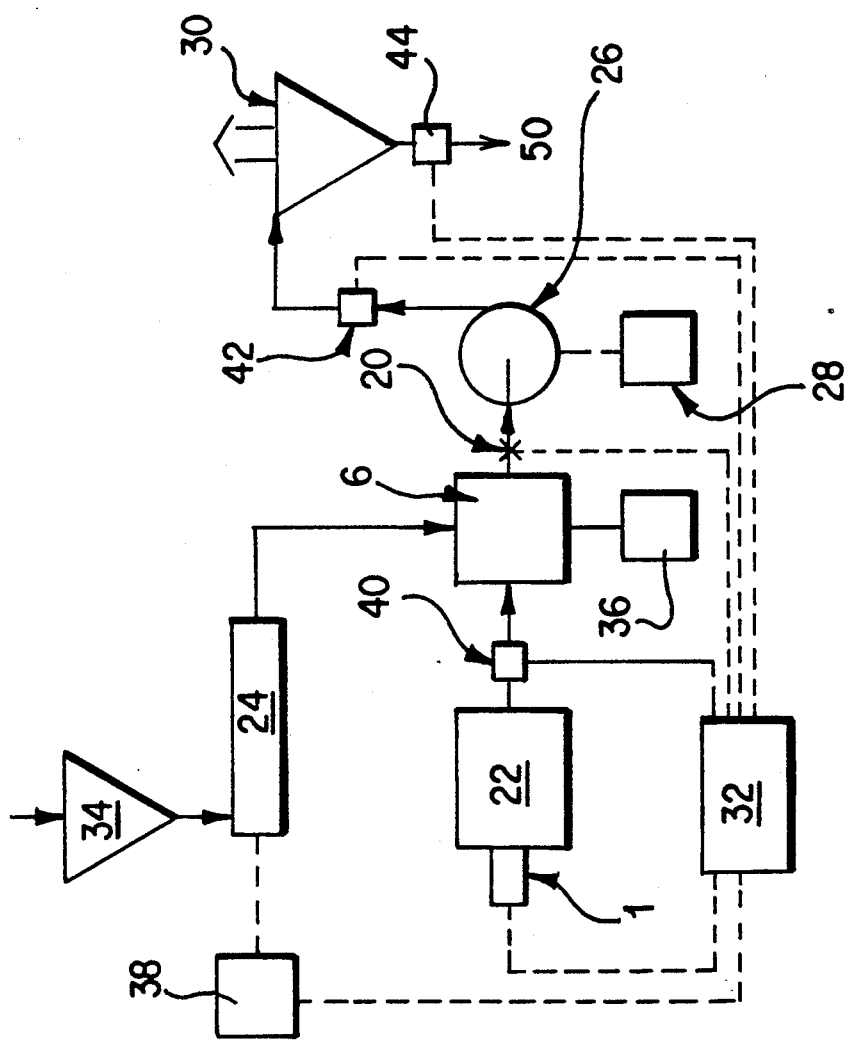
FIG. 1 is a schematic diagram of a system in which the apparatus and process of the invention are used.
Figure 2:
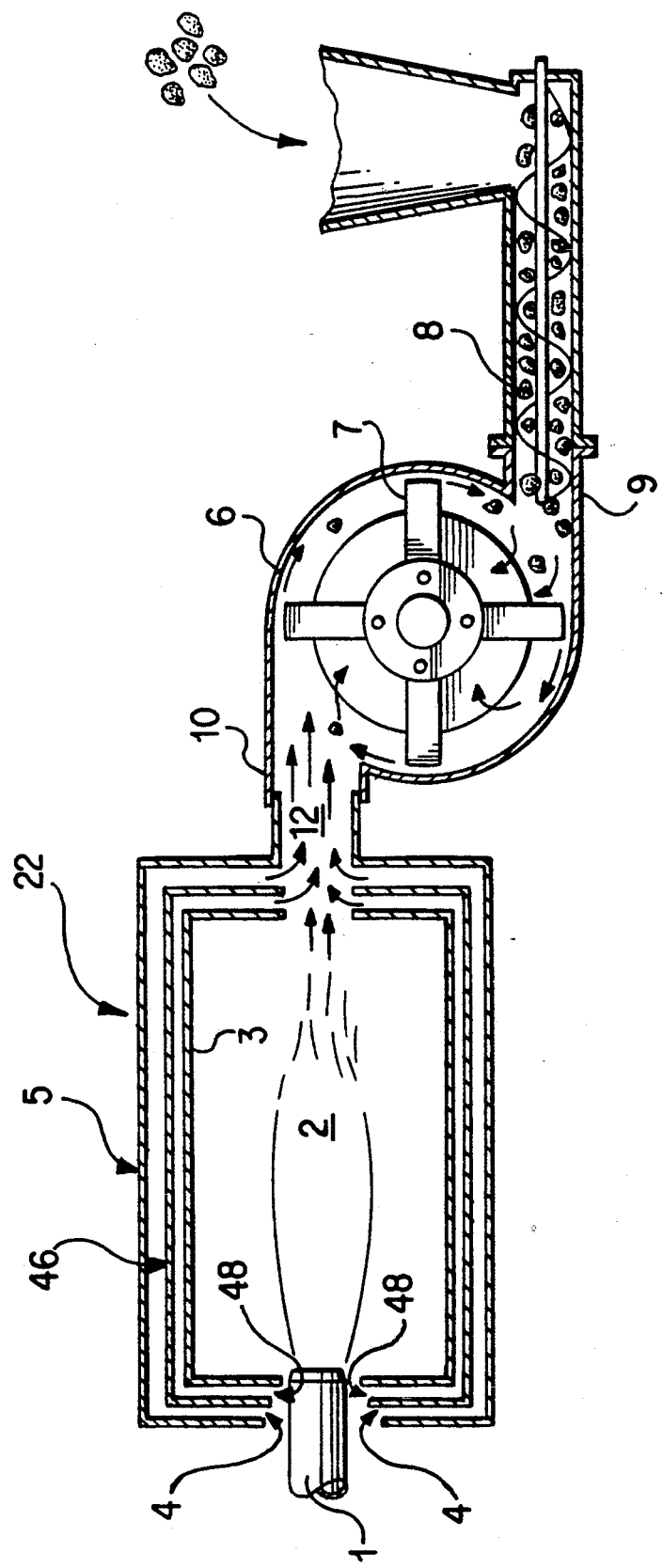
FIG. 2 is a top view of a preferred apparatus of the invention, including a gas source.

With reference to FIGS. 1 and 2, the apparatus of the invention generally comprises an improved material mill-dehydrator wherein the material 8 and hot gas 12 are both tangentially introduced into a chamber 6 at two opposing inlets which are preferably located approximately 160° to 200° (more preferably about 180°) opposite of each other. As shown in FIG. 2, the material 8 is introduced into the chamber 6 via the first inlet 9. The hot gas 12 is introduced into the chamber 6 via the second inlet 10. The chamber 6 includes at least one instrument 7 such as a type of paddle wheel or other rotor that rotates around a shaft 13 in the chamber 6.

By providing the first and second inlets opposite of each other it is possible to reduce the turbulence of the material 8 as it enters the chamber 6. It is believed that reducing the turbulence of the material 8 in this manner allows better control of the material path within the chamber 6 (which optimizes the predictability and reproducibility of system results). In addition, the reduced turbulence in the chamber 6 tends to reduce the energy required to rotate the shaft 13 in the chamber 6.

Providing the first and second inlets opposite of each other in the chamber 6 may tend to reduce charring of the material caused by contact of raw material with hot gases. The charring is reduced because the raw material tends to mix with gas and other materials in the chamber 6 prior to contacting the hot gas entering chamber 6. In other words, since the raw material enters the chamber 6 via the first inlet 9, it has an opportunity to mix with material already in the chamber 6 (which is at a lower temperature than the hot gas) before contacting the higher temperature hot gas entering into the chamber 6 via inlet 10.

An orifice 20 is connected on the exit of the chamber 6. The size of orifice 20 may be varied to cause system parameters to change. For instance, decreasing the size of the orifice 20 will generally result in decreasing the size and moisture content of material particulate exiting the chamber (and vice versa). The chamber 6 may be used with a gas source 22 (e.g., a furnace), a material feed mechanism 24, an exhauster 26 with an exhauster motor 28, a separator 30, and a control system 32.

In operation, the material to be processed is generally deposited into a hopper 34 and then preprocessed into particles of substantially uniform size. The preprocessing may also include heating and pressing the material to remove excess oil and water (not shown in the Figures).

The preprocessed material is then sent by a material feed mechanism 24 (driven by material feed motor 38) into a chamber 6 via a first inlet 9. In the chamber 6 the material 8 is mixed with hot gas 12 from a gas source 22 and simultaneously dried and ground into a powder, pellet, or flake of the desired size and moisture content. The shaft 13 is driven by the chamber motor 36.

After the material has been converted into the desired powder, pellet, or flake, it is then aerodynamically conveyed, by an exhauster 26 driven by a motor 28, to a cyclone or dust separator 30 where the finished powder is separated from the hot gases and water vapor.

A control system 32 may be incorporated into the system for sensing information such as the temperature, moisture content, and size of the material as it exits from the mill-dehydrator, exhauster, or separator. It is to be understood that the temperature, moisture content, and size sensors may be utilized at any point in the system to provide input information for the system control. As shown in FIG. 1, in a preferred embodiment the system includes a temperature sensor 40 to sense the temperature of the hot gas exiting the gas source 22. A second temperature sensor 42 may also be used on the outlet of the exhauster 26. A moisture sensor 44 is shown in FIG. 1 on the outlet of the separator 30. The material feed motor 38 is also connected to the control system 32. System variables such as gas source 22 temperature, material feed rate, or orifice size may then be varied as a function of such information.

With reference to FIG. 2, preferably the gas source comprises a conventional fuel burner 1 which produces a flame envelope 2 inside the inner gas source chamber 3. The products of combustion of the burning fuel exit the inner gas source chamber 3 and mix with ambient air from air passageway 48 (located between the shield 46 around the inner gas source chamber 3) and air passageway 4 (located between the outer shell 5 and the radiation shield 46). The ambient air flows through air passageways 4 and 48 and becomes heated before mixing with the hot gases from the inner gas source chamber 3.

Ambient air flows through air passageways 48 and 4 and mixes with hot gases from the inner source chamber 3. In this manner the gas source 22 is more energy efficient since less heat is lost to the surroundings. The shield 46 reflects heat radiating from the inner gas source chamber 3, while the shell 5 primarily recovers heat conducted from the heat radiation shield 46.

The gas source 22 may be further improved by building the gas source 22 from materials which have a relatively low specific heat and a relatively high thermal conductivity. In this context, "low specific heat" means that preferably the specific heat of such materials is less than that of carbon steel. Similarly, "high thermal conductivity" means that the thermal conductivity of such materials greater than that of carbon steel. By building the gas source 22 in this manner heat storage in the gas source 22 itself (such as is found in refractory-lined furnaces) may be minimized.

The low specific heat and the high thermal conductivity of resulting gas source 22 provides a more rapid response to the temperature control system. As such, the drying process may be more accurately controlled and the finished product may be of a more uniform and high quality. Furthermore, start-up and cool-down time for the gas source are thereby shortened, saving time and energy, and increasing machine volumetric efficiency. In addition to the above, a short cool-down time tends to reduce or eliminate coking of the residual fuel in the fuel nozzles, thus eliminating nozzle clogging and downtime to clean clogged nozzles.

Another aspect of this invention is the addition of a variable area orifice 20 at the chamber 6 exit. The variable orifice 20 may be controlled by a moisture or size sensor to assure that the moisture content and/or particulate size of the finished product is maintained at the desired level without varying the fuel flow rate. In this manner the maximum capacity of the apparatus is thus maintained at all times.

As the mixture 12 of hot combustion gases and ambient air leaves the gas source 22 they are drawn into the chamber 6 via second inlet 10. The mixture 12 enters tangentially to, and in the same direction of motion as the ends of the rapidly rotating instrument 7. At the same time, the material to be processed 8 enters the chamber 6 in a direction that is tangentially to, and in the same direction of motion as the ends of the rotating instrument 7. The material 8 enters the chamber 6 through the first inlet 9 which is located oppositely across the chamber from the second inlet 10.

As the material 8 enters the chamber 6 it is struck by the rapidly rotating instrument 7 and it is whirled around inside the chamber 6. Because of the centrifugal force generated by this rotation, the material is thrown against the inside wall of the chamber 6 where most of its momentum is dissipated as destructive energy or heat. The momentum that is converted into destructive energy fractures the material particles and grinds them into increasingly smaller particulate. This fracturing and grinding separates the dry, outer layers of the material from the wet inner layers so that the dry material can be carried out of the chamber 6 by a gas stream. The momentum that is converted into heat contributes to the dehydrating heat already brought into the chamber 6 with the hot gas. Lastly, the momentum that is retained forces some of the particles to rebound off the wall of the chamber 6 and back into the paths of the instruments 7 where they are again struck by the instruments 7 and thrown against the wall of the chamber 6 to continue the process of fracturing, grinding, and drying.

Figure 3:
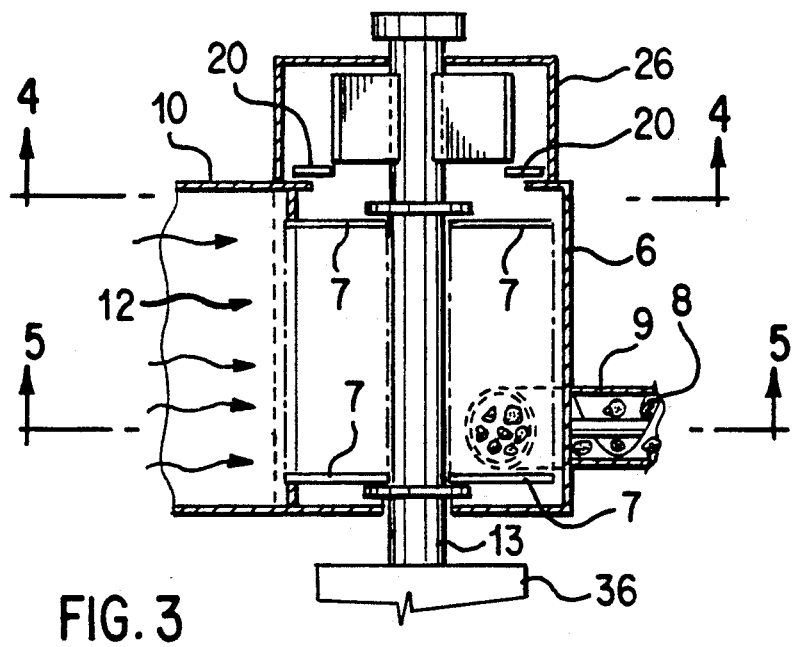
FIG. 3 is a side view of a preferred chamber and exhauster of the invention.
Figure 4:
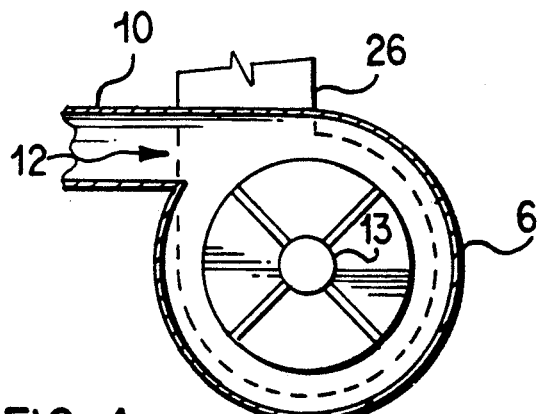
FIG. 4 is a first cross-sectional view of the apparatus shown in FIG. 3.
Figure 5:
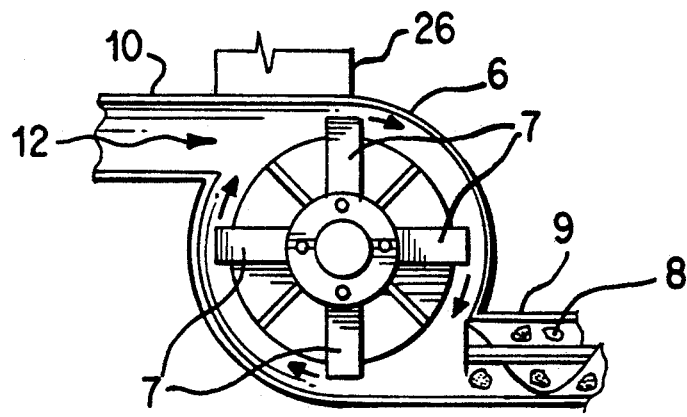
FIG. 5 is a second cross-sectional view of the apparatus shown in FIG. 3.

As the rapidly rotating unfinished particles alternately strike the rapidly moving instruments 7 and rebound off the chamber 6 wall, they follow a radially zig-zag path around the periphery of the chamber 6. Meanwhile the finished particles, air, and water vapors are drawn out of the chamber 6 through the variable orifice 20 by the exhauster 26. As shown in FIGS. 3-5, in a preferred embodiment of this invention the chamber motor 36 drives both the shaft 13 and the exhauster 26. Alternately, the shaft 13 and the exhauster 26 may each be driven by individual motors.

In a preferred embodiment, the finished particles, hot gases, and water vapor are pneumatically conveyed to the dust separator 30 where the hot gases and water vapor are exhausted into the atmosphere while the finished product is directed into storage 50.

Preferably the temperatures of the hot gas entering the chamber 6 via the second inlet 10 range from about 200° to 1500° F. (about 93° to 816° C.) (more preferably about 500° to 1000° F. (about 260° to 538° C.)). Higher temperatures may be used in larger chambers with increased efficiency and capacity.

Preferably the apparatus and process of the invention is used for organic materials. The invention may be used for milling and/or dehydrating organic and organic waste products such as fish scraps from commercial processing of crabs, fish, shrimp, etc., as well as organic waste products from other food processing operations such as vegetable and fruit waste. Examples of organic materials that may be processed by this apparatus and process are vegetables, meats for baby food, and other materials for human consumption where high protein content are desired. Examples of organic waste products that may be processed by this apparatus and process are scraps from commercial processing of fish, shell fish, poultry, livestock, fruits and vegetables and other similar products. Other organic waste products that may also be processed by this apparatus and process are organic materials from municipal garbage, livestock manure, human sludge, and medical waste.

An exit temperature of chamber 6 of about 200° to 500° F. (about 93° to 260° C.), depending on moisture content of the finished product desired, is preferred. In general, lower outlet temperatures from chamber 6 produce a higher moisture content finished product. In a preferred embodiment such outlet temperature may be sensed and the fuel flow to the gas source 22 (the amount of which dictates the temperature of the hot gas entering the chamber 6 via the second inlet 10) may in turn be varied as a function of chamber 6 outlet temperature.

In a preferred embodiment the raw material feed rate may be controlled and limited by sensing the power load on the chamber motor 36, and then varying the material feed rate to the chamber accordingly. In this manner the rate of rotation of the shaft 13 within the chamber 6 may be maintained, thus preventing overload of the motor 36.

It is anticipated that the apparatus and process of the invention will be useful for environmental waste treatment. For instance, system conditions may be adjusted such that bacteria and other microorganisms may be killed at the high temperatures in the chamber 6, thereby rendering the invention useful for treating and sterilizing medical wastes (e.g., medical gloves, hypodermic needles, tissue, gauze, plastics, etc.). In addition, certain chemicals may be neutralized, degraded, or vaporized through treatment by the apparatus and process of the invention. Thus, sludge, sewage, municipal wastes, used oil filters, DDT, HCN, dioxins and other contaminated and harmful materials may also be treated in like manner to render such materials inert for disposal in landfills or further treatment.

EXAMPLE

The invention has been tested using organic waste products such as fish scraps from commercial processing of crabs, fish, shrimp, etc. for the material to be milled and dehydrated. Results were compared to the results obtained from similar experiments with the "fourth type" of apparatus described in the "Prior Art" section of this application. In the fourth type of apparatus wherein the temperature of the hot gas was maintained at about 950° F. (about 510° C.), the moisture content of the finished product was about 8%, the ash content averaged about 30%, and the protein content averaged about 43%. In this apparatus, the feed rate of the material entering the chamber (mill) was reset manually and periodically to maintain the flow of material within limits that allowed the chamber outlet temperature to be held at about 450° F. (about 232° C.) with minimum operation of fuel control.

The present invention was tested with similar materials to compare operating efficacy with the fourth type of apparatus. In the tested embodiment of the invention the moisture content of the milled and dehydrated material was monitored to control the diameter of orifice 20. As a result the chamber 6 outlet temperature was maintained at about 450° F. (about 232° C.) and the finished material moisture content held constant at about 8% regardless of changes in the moisture content of the raw material entering the chamber 6. In other words, when the moisture content of the raw material increased, it was not necessary to increase the chamber 6 temperature (and thereby increase the ash percentage) in order to maintain the 8% moisture content of the finished material. Instead, the material was only held for a longer period of time inside the chamber 6 by the reduction of the diameter of orifice 20, thus providing time for the added moisture to be removed.

Similarly, when it was necessary (or desired) to change the particle size of the finished product, the orifice 20 diameter was varied, thus varying the size of the particles exiting the chamber 6. The chamber 6 outlet temperature was adjusted simultaneously to maintain the desired moisture content of the material exiting the system.

Preliminary tests indicate that the use of the invention will produce improved quality and quantity over presently known mill-dehydrators. When processing fish scraps from commercial processing of crabs, fish, shrimp, etc. as was done for the fourth type of apparatus (see above), the ash content of the finished product was reduced by about 50% (to about 10-20% of total finished product weight), while protein was increased by about 10% (to about 46-50% of total finished product weight).

In addition to the above, when a 28 inch (about 71 centimeter) diameter orifice was used in a 30 inch (about 76 centimeter) diameter chamber, then the particle sizes were about the size of grains of sand. When a 24 inch (about 61 centimeter) diameter orifice was used in the same chamber, then the particle sizes were about that of talcum powder.

The meat and shell sizes of the finished product also varied depending on system conditions. For instance, when the shell particle sizes were about that of grains of sand, then the meat particle sizes were about that of talcum powder. When the shell particle sizes were about 4-10 times larger than grains of sand, then the meat particle sizes were about that of grains of sand. It is possible to screen the meat and shell finished materials based on density and/or particle sizes to separate the meat from the shell.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein, or in the steps, or in the sequence of steps of the methods described herein without departing from the spirit and the scope of the invention as described in the following claims.

We claim:

1. An apparatus for milling, drying, or sterilizing a material, comprising:
   a cylindrical chamber housing;
   at least one rotor rotatably mounted and axially aligned in the chamber;
   a first inlet of the chamber adapted to supply material during use tangentially to the chamber such that the material enters the chamber during use in the same direction as the rotation of the rotor;
   a second inlet of the chamber adapted to supply hot gas during use tangentially to the chamber such that gas enters the chamber during use in the same direction as the rotation of the rotor; and
   an outlet orifice of the chamber substantially axially aligned at one end of the chamber and adapted for allowing material to exit the chamber.

2. The chamber of claim 1 wherein the chamber is substantially cylindrical.

3. The apparatus of claim 1 wherein the first inlet is connected at a first point in the chamber, and the second inlet is connected at a second point in the chamber opposed from the first point.

4. The apparatus of claim 3 wherein the second point is connected about 160° to 200° from the first point.

5. The apparatus of claim 1 wherein the orifice size is variable.

6. The apparatus of claim 1, further comprising a moisture sensor connected adjacent the orifice to sense the moisture content of the material that exits the orifice during use.

7. The apparatus of claim 6 wherein the orifice size is variable as a function of the moisture content of the material that exits the chamber during use.

8. The apparatus of claim 1, further comprising a size sensor positioned adjacent the orifice to sense the size of material particulate that exit the orifice during use.

9. The apparatus of claim 8 wherein the orifice size is variable as a function of the size of the material particulate that exit the chamber during use.

10. The apparatus of claim 1 wherein the gas is supplied to the chamber from a gas source comprising:
    a combustion section with a burner device at a first end and an outlet at a second end connected for flow of hot gas from the gas source to the second inlet of the chamber; and
    a first outer shell which substantially surrounds the combustion section and is separated from the combustion section by an air passageway, and wherein the shell comprises an inlet on a first end for flow of ambient air into the air passageway, and an outlet on a second end for flow of air from the air passageway to the second inlet of the chamber.

11. The apparatus of claim 10 wherein the gas source further comprises a thermal radiation shield between the combustion section and the shell.

12. The apparatus of claim 11, further comprising an air passageway between the shell and the shield connected to allow flow of ambient air through such air passageway to the second inlet of the chamber during use.

13. The apparatus of claim 12 wherein the shield is operable to reflect heat radiated from the combustion section and transfer heat to the air passageway between the combustion section and the shield during use.

14. The apparatus of claim 10 wherein the gas source comprises materials which have a relatively low specific heat.

15. The apparatus of claim 10 wherein the gas source comprises materials which have a relatively high thermal conductivity.

16. The apparatus of claim 1, further comprising an exhauster for withdrawing gas and material from the chamber during use.

17. The apparatus of claim 16 wherein the exhauster is located on the opposite end of the chamber from the first inlet.

18. The apparatus of claim 1 wherein the first inlet is located adjacent one end of the chamber and the second inlet extends substantially along the length of the chamber.

19. The apparatus of claim 1 wherein a motor powers the drive shaft, and further comprising a material feed control operable to vary the rate of material flow to the chamber as a function of power used by the motor.

20. The apparatus of claim 1 wherein at least one rotor comprises an outer end closely adjacent to the inner wall of the chamber.

21. A process of milling, drying, or sterilizing a material, comprising the following steps:
tangentially introducing material into a cylindrical having at least one rotating instrument(s) such that the material enters the chamber in the same direction as the rotation of the instruments;
tangentially introducing hot gas into the chamber such that the gas enters the chamber in the same direction as the rotation of the instruments and the material is dried and reduced in size by contacting the hot gas and the instruments.

22. The process of claim 21, further comprising the step of removing the material and gas from the chamber through an orifice exit.

23. The process of claim 22, further comprising the step of varying the orifice size as a function of moisture content in the materials exiting the chamber.

24. The process of claim 22, further comprising the step of varying the orifice size as a function of the size of the materials exiting the chamber.

25. The process of claim 21, further comprising the step of varying the rate of material flow to the chamber as a function of the amount of power used to rotate the rotating instruments.

26. The process of claim 21 wherein the material is introduced into the chamber at a first point, and the gas is introduced into the chamber at a second point opposite of the first point.

27. A dried and milled material produced according to the process of claim 21.

* * * * *